United States Patent
Lousenberg

(10) Patent No.: US 8,592,630 B2
(45) Date of Patent: Nov. 26, 2013

(54) PROCESSES FOR SEPARATING COMPONENTS IN ALKYL PERFLUOROALKENE ETHER PRODUCTION

(71) Applicant: E I Du Pont De Nemours and Company, Wilmington, DE (US)

(72) Inventor: Robert D Lousenberg, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/627,024

(22) Filed: Sep. 26, 2012

(65) Prior Publication Data

US 2013/0079558 A1    Mar. 28, 2013

Related U.S. Application Data

(60) Provisional application No. 61/539,073, filed on Sep. 26, 2011.

(51) Int. Cl.
C07C 209/86    (2006.01)
C07C 41/06     (2006.01)

(52) U.S. Cl.
USPC ...................................................... 564/296

(58) Field of Classification Search
None
See application file for complete search history.

(56) References Cited

U.S. PATENT DOCUMENTS

2010/0209600 A1*  8/2010  Bartelt et al. ................. 427/127

OTHER PUBLICATIONS

Stojanowa-Antoszczyszyn, M. et al. Dokladi na Bulgarskata Akademiya na Naukite (2003), 56(1), 49-54.*
International Search Report and Written Opinion, PCT/US2012/057382, Jan. 18, 2013.
Naik et al., Phase transfer catalysis: chemistry and engineering, AICHE Journal, 44(3) 1998, 612-646.
Wang et al., Preliminary study on the role played by the third liquid phase in phase transfer catalysis, Chemical Engineering Science, 43(8), 1988, 2019-2024.
U.S. Appl. No. 61/539,073, filed Sep. 26, 2011.
U.S. Appl. No. 13/187,637, filed Jul. 21, 2011.

\* cited by examiner

*Primary Examiner* — Johann R Richter
*Assistant Examiner* — Medhanit Bahta

(57) ABSTRACT

Disclosed are processes for reacting a perfluorinated olefin with an alcohol, an alkali metal hydroxide, and water in the presence of a phase transfer catalyst to form a reaction product mixture that separates into an aqueous phase and an organic phase. Alcohol may be present in an effective amount sufficient to form a third phase comprising at least 50% of the phase transfer catalyst. The third phase can be separated from the organic phase. Also disclosed are methods for recovering and recycling the phase transfer catalyst used in the reaction.

26 Claims, No Drawings

PROCESSES FOR SEPARATING COMPONENTS IN ALKYL PERFLUOROALKENE ETHER PRODUCTION

CROSS REFERENCE(S) TO RELATED APPLICATION(S)

This application claims the benefit of priority of U.S. Provisional Applications 61/539,073, filed Sep. 26, 2011.

BACKGROUND INFORMATION

1. Field of the Disclosure

This invention relates to processes for separating components in the production of unsaturated fluorocarbon ethers. The invention further relates to processes for recovering catalysts used in the production of unsaturated fluorocarbon ethers. The invention also relates to processes for removing water from crude products formed during production of unsaturated fluorocarbon ethers.

2. Description of the Related Art

Chlorofluorocarbon (CFC) compounds have been used extensively in the area of semiconductor manufacture to clean surfaces such as magnetic disk media. However, chlorine-containing compounds such as CFC compounds are considered to be detrimental to the Earth's ozone layer. In addition, many of the hydrofluorocarbons used to replace CFC compounds have been found to contribute to global warming. As a suggested replacement for such CFC compounds, novel alkyl perfluoroalkene ethers were disclosed in U.S. patent application Ser. No. 13/187,637 and U.S. Patent Application Publication No. US 2010/0209600 A1, both of which are incorporated in their entirety herein.

It has been discovered by the inventor that present processes for producing alkyl perfluoroalkene ethers may result in a heterogeneous rag layer that forms between an aqueous phase and an organic phase. This rag layer is believed to form due to the insolubility of the phase transfer catalyst that is used in the reaction. The phase transfer catalyst may be poorly soluble in both aqueous and organic solutions. It has been discovered through experimentation that a rag layer forms in the area between the aqueous phase and the organic phase, rendering separation of the phases more difficult. Furthermore, when used in a continuous operation, the rag layer may increase in size, which may require the reaction to be stopped so that the rag layer may be removed from the separator.

It is therefore desirable in the art to find processes for producing alkyl perfluoroalkene ethers without forming a rag layer. Furthermore, it may also be desirable to have a continuous process for producing alkyl perfluoroalkene ethers. It may also be desirable to have a process for recovering the phase transfer catalyst used in the production of alkyl perfluoroalkene ethers.

SUMMARY

In at least one embodiment of the present disclosure, a process comprises:
  a. contacting a perfluorinated olefin with an alcohol, an alkali metal hydroxide, and water in the presence of a phase transfer catalyst for a period of time to produce a reaction product mixture that separates into an aqueous phase and an organic phase, wherein the alcohol is present in an effective amount sufficient to form a third phase comprising at least 50% of the phrase transfer catalyst; and
  b. separating the third phase from the organic phase.

In at least one other embodiment of the present disclosure, a process comprises:
  a. contacting a perfluorinated olefin with an alcohol, and alkali metal hydroxide, and water in the presence of a phase transfer catalyst for a period of time to produce a reaction product mixture that separates in an aqueous phase and an organic phase; and
  b. adding an additional amount of alcohol to the reaction product mixture, wherein the additional amount of alcohol forms a third phase comprising at least 50% of the phase transfer catalyst initially present.

In accordance with at least one embodiment of the present disclosure, a continuous process comprises:
  a. feeding a reactant stream comprising a perfluorinated olefin, an alcohol, an alkali metal hydroxide, water, and a phase transfer catalyst to a reactor to form a reaction product mixture;
  b. transferring the reaction product mixture from the reactor to a separator;
  c. adding an additional amount of alcohol to the reaction product mixture before the reaction mixture enters the separator, wherein the additional amount of alcohol is added in an amount sufficient to prevent the formation of a rag layer during separation; and
  d. separating an organic phase of the reaction product mixture from the remainder of the reaction product mixture in a continuous decanter, wherein the remainder of the reaction product mixture comprises an aqueous phase.

In at least one embodiment of the present disclosure, a process comprises:
  a. contacting a perfluorinated olefin with an alcohol, an alkali metal hydroxide, and water in the presence of a phase transfer catalyst for a period of time to produce a reaction product mixture that separates into an organic phase and an aqueous phase;
  b. adding an additional amount of alcohol to the reaction product mixture, wherein the additional amount of alcohol forms a third phase comprising at least 50% of the phase transfer catalyst;
  c. separating the third phase from the organic phase and the aqueous phase; and
  d. recovering the phase transfer catalyst from the third phase.

The foregoing general description and the following detailed description are exemplary and explanatory only and are not restrictive of the invention, as defined in the appended claims.

DETAILED DESCRIPTION

Before addressing details of embodiments described below, some terms are defined or clarified.

For purposes of the present invention, a "phase transfer catalyst" is a substance that facilitates the transfer of ionic compounds (e.g., reactants or components) into an organic phase. The phase transfer catalyst facilitates the reaction of these dissimilar and incompatible components. While various phase transfer catalysts may function in different ways, their mechanism of action is not determinative of their utility in the present process.

As used herein, the term "alcohol" is used to refer to low alcohols, such as, for example, methanol and ethanol.

As used herein, the phrase "reaction product" means the desired product of the reaction, such as, for example, unsaturated fluoroethers. The phrase "reaction product mixture" is used herein to refer to the reaction product plus other reaction byproducts and leftover reactant, i.e., the contents of the reactor after the reaction has taken place.

As used herein, the term "phase" means an immiscible partition formed from a mixture of components. For example, the phrases "organic phase" and "aqueous phase" refer to two separate partitions, one containing organic material and the other being water based. The phrase "third phase" refers to a third partition independent from the organic and aqueous phases.

According to at least one embodiment, the reaction products disclosed herein are unsaturated fluoroethers which may have utility as solvents, carrier fluids, dewatering agents, degreasing solvents or defluxing solvents. The reaction products may comprise alkyl perfluoroalkene ethers, such as, for example, methyl perfluoropentene ethers (MPPE) or methyl perfluoroheptene ethers (MPHE). Other alkyl perfluoroalkene ethers may also be produced in accordance with the present teachings, as one skilled in the art would readily appreciate.

In at least one embodiment, the reaction product disclosed herein may be prepared by contacting a perfluoroalkene, such as perfluoro-3-heptene, peflouro-2-heptene, perfluoro-2-hexene, perfluoro-3-hexene, or perfluoro-2-pentene with an alcohol in the presence of a strong base. For example, perfluoro-3-heptene may be reacted with an alcohol such as methanol or ethanol, or mixtures thereof, in the presence of an aqueous solution of a strong base to produce unsaturated fluoroethers.

According to at least one embodiment, the products from the reaction of perfluoro-3-heptene with methanol comprise 5-methoxyperfluoro-3-heptene, 3-methoxyperfluoro-3-heptene, 4-methoxyperfluoro-2-heptene and 3-methoxyperfluoro-2-heptene.

In at least one embodiment, the products from the reaction of perfluoro-2-pentene with methanol comprise 4-methoxyperfluoro-2-pentene, 2-methoxyperfluoro-2-pentene, 3-methoxyperfluoro-2-pentene, and 2-methoxyperfluoro-3-pentene.

In accordance with at least one further embodiment, the products from the reaction of perfluoro-2-octene with methanol comprise cis- and trans-2-methoxyperfluoro-2-octene and 2-methoxyperfluoro-3-octene.

In at least one embodiment, the strong base is a base which will react with an alcohol to produce an alkoxide upon combination of the base with said alcohol. Non-limiting examples of bases which can be used to form such alkoxides include alkali metal hydroxides, such as sodium hydroxide or potassium hydroxide.

In at least one embodiment, the strong base is present in the form of an aqueous solution having a concentration of alkali metal hydroxide of from 10% by weight to 45% by weight. In other embodiments, one mole of alkali metal hydroxide is used per mole of alcohol to produce the alkoxide.

In at least one other embodiment, 1.1 moles of alkali metal hydroxide per mole of alcohol is used. In yet other embodiments, about 0.9 moles of alkali metal hydroxide per mole of alcohol is used. One skilled in the art would recognize that other molar ratios may also be used based on the reactants, the desired product, the reaction conditions, etc.

In at least one embodiment, one mole of alkali metal hydroxide is used per mole of perfluoroalkene. In other embodiments, about 1.1 moles of alkali metal hydroxide are used per mole of perfluoroalkene. In yet other embodiments, about 1.05 moles of alkali metal hydroxide are used per mole of perfluoroalkene. One skilled in the art would recognize that other molar ratios may also be used based on the reactants, the desired product, the reaction conditions, etc.

According to at least one embodiment, the alkali metal hydroxide is combined with the perfluoroalkene, and then an alcohol and water are added to the mixture of perfluoroalkene and base, resulting in an immediate exothermic reaction. In another embodiment, the alkali metal hydroxide is dissolved in water and mixed with the perfluoroalkene. Addition of the alcohol results in an immediate exothermic reaction to produce the unsaturated fluoroethers.

In at least one embodiment, the alcohol is added to the perfluoroalkene, alkali metal hydroxide and water in one portion. In another embodiment, the alcohol is added slowly over a period of time. In one embodiment, the alcohol is added over one hour. In another embodiment, the alcohol is added over two hours. In yet another embodiment, the perfluoroalkene, alkali metal hydroxide and alcohol are added together, and the water is added slowly over time.

In accordance with at least one embodiment, the perfluoroalkene, alkali metal hydroxide, alcohol and water are all added at about room temperature. In another embodiment, the perfluoroalkene and aqueous solution of alkali metal hydroxide are heated to about 50° C., and the alcohol is added slowly over a period of time.

In at least one embodiment of the present disclosure, a phase transfer catalyst is added to the mixture of perfluoroalkene, alkali metal hydroxide, alcohol, and water. In at least one embodiment, the phase transfer catalyst is chosen from onium salts and derivates and mixtures thereof.

Onium salts include quaternary phosphonium salts and quaternary ammonium salts that may be used as the phase transfer catalyst in the process of the present invention; such compounds can be represented by the following formulas I and II:

$$R^1R^2R^3R^4P^{(+)}X'^{(-)} \qquad (I)$$

$$R^1R^2R^3R^4N^{(+)}X'^{(-)} \qquad (II)$$

wherein each of $R_1$, $R_2$, $R_3$ and $R_4$, which may be the same or different, is an alkyl group, an aryl group or an aralkyl group, and X' is a halogen atom. Specific examples of these compounds include tetramethylammonium chloride, tetramethylammonium bromide, benzyltriethylammonium chloride, methyltrioctylammonium chloride (available commercially under the brands Aliquat® 336 and Adogen® 464), tetra-n-butylammonium chloride, tetra-n-butylammonium bromide, tetra-n-butylammonium hydrogen sulfate, tetra-n-butylphosphonium chloride, tetraphenylphosphonium bromide, tetraphenylphosphonium chloride, triphenylmethylphosphonium bromide and triphenylmethylphosphonium chloride. Among them, benzyltriethylammonium chloride is preferred for use under strongly basic conditions. Other useful compounds within this class of compounds include those exhibiting high temperature stabilities (e.g., up to about 200° C.) and including 4-dialkylaminopyridinium salts such as tetraphenylarsonium chloride, bis[tris(dimethylamino)phosphine]iminium chloride and tetratris[tris(dimethylamino)phosphinimino]phosphonium chloride; the latter two compounds are also reported to be stable in the presence of hot, concentrated sodium hydroxide and, therefore, can be particularly useful.

In at least one further embodiment, the phase transfer catalyst is chosen from quaternary ammonium salts and quaternary phosphonium salts. In at least one embodiment, the phase transfer catalyst is Aliquat® 336. Aliquat® 336 is a mixture of mostly methyltrioctylammonium and a small amount of methyltridecylammonium.

In at least one embodiment, the amount of phase transfer catalyst ranges from about 1% by weight to about 10% by weight of the alkali metal hydroxide. An effective amount of the phase transfer catalyst should be used in order to effect the desired reaction; such an amount can be determined by one of ordinary skill in the art by limited experimentation once the reactants, process conditions and phase transfer catalyst are selected.

In at least one embodiment of the present disclosure, a process comprises:
 a. contacting a perfluorinated olefin with an alcohol, an alkali metal hydroxide, and water in the presence of a phase transfer catalyst for a period of time to produce a reaction product mixture that separates into an aqueous phase and an organic phase, wherein the alcohol is present in an effective amount sufficient to form a third phase comprising at least 50% of the phase transfer catalyst; and
 b. separating the third phase from the organic phase.

One of ordinary skill in the art would understand how to determine the period of time to produce a reaction product mixture. The period of time is dependent on the reactants, the desired product mixture, the conditions of the reaction, etc., and as such, would be determined by the skilled artisan through routine experimentation.

In at least one embodiment, the effective amount of alcohol present to form a third phase comprising at least 50% of the phase transfer catalyst may range, for example, from 1.1 to 1.5 times the stoichiometric amount necessary for the reaction to go to completion. In embodiments where the reaction does not go to completion, such as, for example, when only 80-85% of the perfluorinated olefin is consumed, lesser amounts of alcohol may be used. In at least one embodiment, the reaction does not go to completion and the alcohol is present in a stoichiometric amount, i.e., the amount that of alcohol that would be needed for the reaction to go to completion.

In at least one embodiment, the alcohol is present in an amount sufficient to form a third phase comprising at least 65% of the phase transfer catalyst. In at least one further embodiment, the alcohol is present in an amount sufficient to form a third phase comprising at least 75% of the phase transfer catalyst, such as at least 85% or 90% of the phase transfer catalyst.

In at least one embodiment of the present disclosure, the third phase has a density lower than the densities of the aqueous phase and the organic phase. In those embodiments, the aqueous phase forms on top of the organic phase, and the third phase forms on top of the aqueous phase.

In at least one embodiment, separating the third phase from the organic phase comprises separation in a continuous decanter. According to at least one embodiment, the third phase and the aqueous phase are separated from the organic phase in a two-phase decanter. The aqueous phase and third phase may be removed from the top of the decanter and the organic phase may be removed from the bottom of the decanter. In other embodiments, a three-phase decanter is used to separate all three phases. In at least one embodiment using a three-phase decanter, the third phase can be removed from the top of the decanter, the aqueous phase can be removed from the middle of the decanter, and the organic phase can be removed from the bottom. One of ordinary skill in the art would recognize that the placement of the outtakes for each phase or combined phases depends on the volume of the decanter, the volumetric ratio of the three phases, the inlet and outlet flow rates, the densities of the three phases, etc.

In at least one embodiment of the present disclosure, the third phase may be separated from the aqueous phase in a separate process.

In accordance with at least one embodiment of the present disclosure, a process comprises:
 a. contacting a perfluorinated olefin with an alcohol, an alkali metal hydroxide, and water in the presence of a phase transfer catalyst for a period of time to produce a reaction product mixture that is separable into an aqueous phase and an organic phase;
 b. adding an additional amount of alcohol to the reaction product mixture, wherein the additional amount of alcohol forms a third phase comprising at least 50% of the phase transfer catalyst initially present.

In at least one embodiment of the present disclosure, the additional amount of alcohol may be added to the reaction product mixture after the reactants has ended, either by reacting to completion or by ending the reaction before the reactants have been entirely depleted. In other embodiments, the additional amount of alcohol may be present before the reaction begins.

According to at least one embodiment of the present disclosure, a process comprises:
 a. feeding a reactant stream comprising a perfluorinated olefin, an alcohol, an alkali metal hydroxide, water, and a phase transfer catalyst to a reactor to produce a reaction product mixture;
 b. transferring the reaction product mixture from the reactor to a separator;
 c. adding an additional amount of alcohol to the reaction product mixture before the reaction product mixture enters the separator, wherein the additional amount of alcohol is added in an amount sufficient to prevent the formation of a rag layer during separation; and
 d. separating an organic phase of the reaction product mixture from the remainder of the reaction product mixture in a continuous decanter, wherein the remainder of the reaction product mixture comprises an aqueous phase.

In at least one embodiment, the organic phase comprises a heterogeneous azeotrope comprising fluorinated ethers and water. The process may further comprise drying the organic phase to remove the water. In at least one embodiment, the organic phase is dried by distilling the heterogeneous azeotrope to separate the water from the fluorinated ether product. In at least one further embodiment, distilling the heterogeneous azeotrope comprises separating unreacted perfluorinated olefin and water from an intermediate mixture, followed by further separating the intermediate mixture into byproducts and saturated ethers in a second distillation.

In at least one embodiment, the intermediate mixture comprises less than 0.1% by weight perfluorinated olefin. In further embodiments, the intermediate mixture comprises less than 0.05% perfluorinated olefin, or less than 0.01% perfluorinated olefin.

In at least one embodiment, the intermediate mixture comprises less than 1% by weight water. According to at least one embodiment, the intermediate mixture comprises less than 50 ppm water. In other embodiments, the intermediate mixture comprises less than 25 ppm water.

In at least one embodiment, the additional amount of alcohol added to the product mixture is about 10% to about 50% of the amount of alcohol present in the reactant stream.

In accordance with at least one embodiment, the process may further comprise separating the remainder of the reaction product mixture to separate the third phase from the aqueous phase. In at least one embodiment, the phase transfer catalyst may be recovered from the third phase by any method known in the art. The recovered phase transfer catalyst can be recycled by adding the recovered phase transfer catalyst back into the reactant stream.

In at least one embodiment of the present disclosure, a process comprises:
 a. contacting a perfluorinated olefin with an alcohol, an alkali metal hydroxide, and water in the presence of a phase transfer catalyst for a period of time to produce a reaction product mixture that is separable into an organic phase and an aqueous phase;
 b. adding an additional amount of alcohol to the reaction product mixture, wherein the additional amount of alcohol forms a third phase comprising at least 50% of the phase transfer catalyst initially present;
 c. separation the third phase from the organic phase and the aqueous phase; and
 d. recovering the phase transfer catalyst from the third phase.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics*, 81$^{st}$ Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting. Unless otherwise specified, percentages disclosed herein are based on weight.

EXAMPLES

The concepts described herein will be further described in the following examples, which do not limit the scope of the invention described in the claims.

Example 1

Continuous Synthesis of methyl perfluoroheptene ethers (MPHE) or methyl perfluoropentene ethers (MPPE)

A Parr® 5100 reactor with utilizing a 650-mL Hasteloy® bomb (2.5" ID, oil jacketed, 590-mL working volume) was modified into a continuous stirred tank reactor (CSTR) as outlined in Figure 1. The existing ¼" OD dip-tube and valve assembly were modified to incorporate a second concentric ¹⁄₁₆" OD inner dip-tube. The inner dip-tube terminated near the bottom of the reactor and was ~2" longer than the outer dip-tube. The CSTR stirrer shaft assembly was fitted with 2×1.375" diameter four bladed propellers for thorough mixing. One blade was mounted at the bottom of the stirrer shaft (~1.5" from the reactor bottom), the second blade was mounted 3.5" higher on the stirrer shaft (approximately 3" from bottom of the bomb head). Separate reservoirs for perfluoroheptene (PFH) or perfluoropentene (PFP), and 45% aqueous potassium hydroxide (KOH) were connected with ⅛" perfluoroalkoxy (PFA) tubing through calibrated FMI® pumps and plumbed to the valve assembly port for the outer dip-tube. A reservoir that contained either methanol with 4% dissolved Aliquat® 336 or 60% aqueous methanol (2.5% dissolved Aliquat® 336) was connected to the valve assembly connection for the inner dip-tube. Calibrated Eldex Laboratories Inc B-100-S and/or FMI® pumps were used to add the methanol to the CSTR.

The CSTR was operated liquid-full at high stirring rates (1000-rpm) to facilitate the heterogeneous reaction. In a typical CSTR start-up, the reactor was partially filled with PFH or PFP and then heated to the desired operating temperature. The KOH and methanol pumps were started and operated for a given time period before restarting the PFH/PFP pump. Reaction stoichiometry and residence times were then controlled using the pump settings. The reactions were exothermic and excess heat was initially removed through an internal water cooling loop and later through the oil jacket, once steady state conditions were achieved. The liquid-full CSTR contents continuously exited through a port at the top of the reactor through ⅛" PFA tubing. The tubing was connected in series through check valves (25 or 50-psig), a 60-μm filter housing, and a sampling tee with valve, before discharging into a decanter that operated continuously by gravity. Some examples of reaction conditions and experimental results are summarized in Table 1 (MPHE synthesis) and Table 2 (MPPE synthesis). Steady state reaction compositions were measured using gas chromatography with mass spectral detection (GC/MS). Compositions were calculated using the total ion signals and were un-calibrated.

TABLE 1

MPHE synthesis

| Exp. | PFH:KOH:MeOH (mole ratios) | Temperature (° C.) | Residence Time (min) | PFH conversion at steady state (%) | Product/saturated ethers at steady state (%) | Higher methanol adducts at steady state (%) |
|---|---|---|---|---|---|---|
| 1 | 1:0.90:1.2 | 80 | 30 | 81.1 | 95.5/1.70 | 2.77 |
| 2 | 1:0.93:1.2 | 80 | 30 | 82.6 | 95.5/1.60 | 2.86 |
| 3 | 1:0.95:1.2 | 80 | 30 | 82.9 | 95.5/1.47 | 3.00 |
| 4 | 1:0.95:1.2 | 80 | 30 | 86.9 | 96.4/1.45 | 2.16 |

TABLE 1-continued

MPHE synthesis

| Exp. | PFH:KOH:MeOH (mole ratios) | Temperature (° C.) | Residence Time (min) | PFH conversion at steady state (%) | Product/saturated ethers at steady state (%) | Higher methanol adducts at steady state (%) |
|---|---|---|---|---|---|---|
| 5 | 1:0.95:1.2* | 80 | 30 | 83.0 | 95.9/1.41 | 2.67 |
| 6 | 1:0.95:1.5* | 80 | 30 | 91.1 | 93.1/1.13 | 5.83 |

*The methanol containing Aliquat ® 336 was pre-diluted to 60% with water.

TABLE 2

MPPE synthesis

| Exp. | PFP:KOH:MeOH (mole ratios) | Temperature (° C.) | Residence Time (min) | PFP conversion at steady state (%) | Product/saturated ethers at steady state (%) | Higher methanol adducts at steady state (%) |
|---|---|---|---|---|---|---|
| 1 | 1:0.75:1.0* | 60 | 30 | 76.6 | 92.2/6.53 | 1.23 |
| 2 | 1:1.0:0.75* | 60 | 30 | 61.5 | 93.3/5.33 | 1.39 |
| 3 | 1:0.75:1.0* | 60 | 30 | 69.5 | 92.7/5.64 | 1.69 |
| 4 | 1:0.75:1.0* | 60 | 30 | 62.3 | 92.8/5.92 | 1.27 |
| 5 | 1:0.75:1.0* | 70 | 30 | 81.4 | 90.8/6.97 | 2.19 |
| 6 | 1:0.75:1.0* | 50 | 30 | 75.1 | 90.2/6.90 | 2.89 |

*The methanol containing Aliquat ® 336 was pre-diluted to 60% with water.

Example 2

Separation of Crude Product and Aqueous Phases and Recovery of the Phase Transfer Catalyst Using Continuous Decanters The product stream exiting the CSTR was separated in a continuous decanter into a bottom organic phase, containing the crude product, and an upper aqueous phase. Two different sized continuous decanters were evaluated as outlined in Table 3; a 1-L glass decanter and a 1-gallon decanter that was made from high density polyethylene. The polyethylene decanter was designed with two side ports so that two different working volumes could be evaluated. Material from the CSTR entered either decanter through a PFA dip tube from the top. The dip tubes terminated subsurface in the decanter at a point 1 to 2 cm below the aqueous-organic interface. The polyethylene decanter also incorporated a right angle elbow at the end of the dip tube to minimize vertical momentum. The separated aqueous phase exited the decanter through a side port near the top while the organic phase exited the decanter at the bottom. Relative phase volumes in the decanters were controlled by the relative height position of the organic phase overflow with respect to the exit port for the aqueous phase. The organic and aqueous phases exiting the decanter were collected under steady state conditions into separate 1-gallon high density polyethylene jugs. The aqueous phase mainly contained potassium salts (KF byproduct and residual KOH) plus some residual MeOH and phase transfer catalyst. Under process conditions where a MeOH excess was present, either in the CSTR or potentially added before the decanter, a small distinct third phase formed on top of the aqueous phase in the decanter. The third phase was later separated and recovered from the aqueous phase and appeared to contain a significant fraction of Aliquat® 336.

TABLE 3

Continuous MPHE decanter operation and results

| | | Decanter | | |
|---|---|---|---|---|
| | | 1-L glass | 1-gal polyethylene | |
| Working Volume (mL) | | 750 | 1800 | 3000 |
| Diameter (cm) | | 5.75 | 15.0 | |
| Flow rates (mL/min)* | Organic phase | | 12.2 | |
| | Aqueous phase | | 7.8 | |
| Vertical velocity (cm/min) | Organic phase | 0.47 | 0.069 | |
| | Aqueous phase | 0.30 | 0.044 | |
| Residence time (min) | Organic phase | 33 | 98 | 159 |
| | Aqueous phase | 45 | 77 | 136 |
| Density (g/mL) at 23° C.) | Organic phase | | 1.60 | |
| | Aqueous phase | | 1.29 | |
| | $3^{rd}$ phase containing Aliquat ® 336 | | 1.08 | |
| Non-volatile residue (w/w) | Organic phase | 1.8% | 520-ppm | 250-ppm |
| Recovered phase content after 3 hours additional standing (% v/v) | Aqueous from organic | 5 | 0.14 | 0.12 |
| | Organic from aqueous | 2.4 | 0.21 | 0.18 |
| Recovered $3^{rd}$ phase containing Aliquat ® 336 vs. aqueous phase (% v/v) | | 1.3 | 2.3 | 3.4 |

*Reactor PFH/KOH/MeOH molar stoichiometry = 1:0.95:1.2.

Two separate accumulations of recovered third phase were characterized and are summarized in Table 4. Quantification from $^1$H NMR showed that both third phase samples contained Aliquat® 336, MPHE, methanol, and water. A quantity of each third phase was also partitioned into water and toluene and the non-volatile residue in the water was measured by gravimetric drying. Inorganic salts such as potassium fluoride, that were not easily distinguishable from Aliquat® 336 by NMR, were expected to partition into the water while the Aliquat® 336 partitioned into the toluene. Furthermore, the measured Aliquat® 336 fractions of 25.7 and 31.0% were factored into the third phase volumes that were recovered from decanter experiments and appeared to converge with the known concentration in the CSTR. The calculated total Aliquat® 336 in the third phase of the 750, 1800, and 3000-mL decanter experiments corresponded to 37 to 43%, 53 to 67%, and 93% to 105% of the Aliquat® 336 in the CSTR, respectively. The majority of the Aliquat® 336 could be isolated and recovered in the third phase given sufficient time for the aqueous and third phases to separate.

TABLE 4

Characterization of third phase samples

| | | Third Phase | | | |
|---|---|---|---|---|---|
| | | Sample 1 | | Sample 2 | |
| Component | Measurement Technique | Wt % | Wt % (normalized) | Wt % | Wt % (normalized) |
| Non volatile residue (total) | Gravimetric drying | 68 ± 1 | | 71 ± 1 | |
| Water | Karl Fisher | 1 to 2 | | 1 to 2 | |
| Aliquat ® 336 | $^1$H NMR | | 25.7 | | 31.0 |
| Methanol | $^1$H NMR | | 5.9 | | 4.9 |
| Water | $^1$H NMR | | 4.1 | | 3.1 |
| MPHE | $^1$H NMR | | 43.9 | | 41.6 |
| Non volatile residue (extract) | Gravimetric drying | | 20.5 ± 1.5 | | 19.3 ± 1.5 |

Example 3

Removal of Residual Water and Methanol in the Crude MPHE Phase by Continuous Distillation of Heterogeneous Azeotropes The crude MPHE product phase that was isolated from the decanter was pumped at approximately 5 to 6-mL/min using an FMI® pump directly into a first continuous distillation apparatus. The apparatus consisted of a 2-L still-pot and 500-Watt heating mantle, 10 and 20-plate 1" ID Oldershaw columns in series, with an adapter for the addition of the crude product installed between the two columns. Columns and adapters were vacuum jacketed and silvered and the top of the column was fitted with a high reflux ratio still head (Claisen type) which incorporated a magnetic take-off valve. The valve was activated by a solenoid, controlled by a digital repeat cycle timer (Ace Glass 6671-14). The distillate take-off port was connected to a 500-mL graduated receiver. A heterogeneous azeotrope distillate (bp=69 to 71° C.) was isolated overhead at a controlled reflux ratio that varied from 20:2 to 60:2 (s/s). The distillate separated in the receiver into two layers and was predominantly PFH with a small aqueous methanol phase (0.12% w/w) on top. The water in the aqueous methanol phase was measured by Karl Fisher titration at 25%. The intermediate crude MPHE (bp=114 to 115° C.) that collected in the still-pot contained less than 0.01% residual PFH by (GC/MS), and less than 25-ppm water (Karl Fisher). The intermediate crude MPHE was then pumped from the still pot into a second similar continuous distillation apparatus were it was further separated overhead from saturated ether and higher methanol adduct byproducts.

Example 4

Removal of Residual Water and Methanol in the Crude MPPE Phase by Continuous Distillation of Heterogeneous Azeotropes The crude MPPE product phase that had been isolated from the decanter was pumped at approximately 5 to 6-mL/min using an FMI® pump directly into the first continuous distillation apparatus as described in example 3. A heterogeneous azeotrope distillate (bp ~24° C.) was isolated overhead at a controlled reflux ratio that varied from 20:2 to 60:2 (s/s). The distillate separated in the receiver into two layers and was predominantly PFP with a small aqueous methanol phase on top. The intermediate crude MPPE (bp=75 to 76° C.) that collected in the still-pot contained less than 0.01% residual PFP by (GC/MS), and less than 25-ppm water (Karl Fisher). The intermediate crude MPPE was then pumped from the still pot into a second similar continuous distillation apparatus were it was further separated overhead from saturated ether and higher methanol adduct byproducts.

Many aspects and embodiments have been described above and are merely exemplary and not limiting. After reading this specification, skilled artisans appreciate that other aspects and embodiments are possible without departing from the scope of the invention. Other features and benefits of any one or more of the embodiments will be apparent from the following detailed description, and from the claims.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. A process comprising:
   a. contacting a perfluorinated olefin with an alcohol, an alkali metal hydroxide, and water in the presence of a phase transfer catalyst for a period of time to produce a reaction product mixture that separates into an aqueous phase and an organic phase, wherein the alcohol is present in an effective amount sufficient to form a third phase comprising at least 50% of the phase transfer catalyst; and
   b. separating the third phase from the organic phase.

2. The process of claim 1, wherein the perfluorinated olefin is perfluoro-3-heptene, pefluoro-2-heptene, perfluoro-2-hexene, perfluoro-3-hexene, perfluoro-2-pentene, or perfluoro-2-octene.

3. The process of claim 1, wherein the phase transfer catalyst is chosen from onium salts and derivatives and mixtures thereof.

4. The process of claim 3, wherein the phase transfer catalyst is chosen from quaternary ammonium salts and quaternary phosphonium salts.

5. The process of claim 3, wherein said phase transfer catalyst is methyltrioctylammonium chloride and methyltridecylammonium chloride.

6. The process of claim 1, wherein said alcohol is chosen from methanol and ethanol.

7. The process of claim 1, wherein the said alcohol is present in an amount with respect to the perfluorinated olefin initially present ranging from about 1.1 to 1.5 times the stoichiometric amount.

8. The process of claim 1, wherein said alkali metal hydroxide is sodium hydroxide or potassium hydroxide.

9. The process of claim 1, wherein the process is a continuous process.

10. The process of claim 9, wherein separating the third phase from the organic phase comprises separating the third phase from the organic phase in a continuous decanter.

11. The process of claim 1, wherein separating the third phase from the organic phase comprises separating the aqueous phase with the third phase.

12. A process comprising:
a. contacting a perfluorinated olefin with an alcohol, an alkali metal hydroxide, and water in the presence of a phase transfer catalyst for a period of time to produce a reaction product mixture that is separable into an aqueous phase and an organic phase;
b. adding an additional amount of alcohol to the reaction product mixture, wherein the additional amount of alcohol forms a third phase comprising at least 50% of the phase transfer catalyst initially present.

13. A continuous process comprising:
a. feeding a reactant stream comprising a perfluorinated olefin, an alcohol, an alkali metal hydroxide, water, and a phase transfer catalyst to a reactor to produce a reaction product mixture;
b. transferring the reaction product mixture from the reactor to a separator;
c. adding an additional amount of alcohol to the reaction product mixture before the reaction product mixture enters the separator, wherein the additional amount of alcohol is added in an amount sufficient to prevent the formation of a rag layer during separation; and
d. separating an organic phase of the reaction product mixture from the remainder of the reaction product mixture in a continuous decanter, wherein the remainder of the reaction product mixture comprises an aqueous phase.

14. The process of claim 13, wherein the organic phase comprises a heterogeneous azeotrope comprising fluorinated ethers and water, and the process further comprises drying the organic phase by distilling the heterogeneous azeotrope to remove the water.

15. The process of claim 14, wherein distilling the heterogeneous azeotrope comprises separating perfluorinated olefin and water from an intermediate mixture in a first continuous distillation apparatus, and further separating the intermediate mixture into byproducts and saturated ethers in a second continuous distillation apparatus.

16. The process of claim 13, wherein the additional amount of alcohol added to the reaction product mixture is added in an amount sufficient to form a third phase comprising at least 50% of the phase transfer catalyst in the reactant stream.

17. The process of claim 16, wherein the additional amount of alcohol added to the product mixture is about 10% to about 50% of the amount of alcohol in the reactant stream.

18. The process of claim 16, wherein the remainder of the reaction product mixture that is separated from the organic phase further comprises the third phase.

19. The process of claim 18, further comprising separating the aqueous phase from the third phase.

20. The process of claim 18, further comprising recovering the phase transfer catalyst in the third phase.

21. The process of claim 13, wherein the perfluorinated olefin is chosen from perfluoro-3-heptene, pefluoro-2-heptene, perfluoro-2-hexene, perfluoro-3-hexene, perfluoro-2-pentene, and perfluoro-2-octene.

22. The process of claim 13, wherein the alcohol is chosen from methanol and ethanol.

23. The process of claim 13, wherein the phase transfer catalyst is chosen from onium salts and derivatives and mixtures thereof.

24. The process of claim 23, wherein the phase transfer catalyst is chosen from quaternary ammonium salts and quaternary phosphonium salts.

25. The process of claim 24, wherein the phase transfer catalyst comprises methyltrioctylammonium chloride and methyltridecylammonium chloride.

26. A process comprising:
a. contacting a perfluorinated olefin with an alcohol, an alkali metal hydroxide, and water in the presence of a phase transfer catalyst for a period of time to produce a reaction product mixture that is separable into an organic phase and an aqueous phase;
b. adding an additional amount of alcohol to the reaction product mixture, wherein the additional amount of alcohol forms a third phase comprising at least 50% of the phase transfer catalyst initially present;
c. separating the third phase from the organic phase and the aqueous phase; and
d. recovering the phase transfer catalyst from the third phase.

* * * * *